United States Patent
Fickel et al.

(10) Patent No.: US 11,041,127 B2
(45) Date of Patent: Jun. 22, 2021

(54) SHALE GAS AND CONDENSATE TO CHEMICALS

(71) Applicant: SABIC GLOBAL TECHNOLOGIES B.V., Bergen op Zoom (NL)

(72) Inventors: Dustin Fickel, Sugar Land, TX (US); Travis Conant, Sugar Land, TX (US); Dick Alan Nagaki, Sugar Land, TX (US); Raul Velasco Pelaez, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/639,215

(22) PCT Filed: Aug. 10, 2018

(86) PCT No.: PCT/US2018/046227
§ 371 (c)(1),
(2) Date: Feb. 14, 2020

(87) PCT Pub. No.: WO2019/036291
PCT Pub. Date: Feb. 21, 2019

(65) Prior Publication Data
US 2020/0255750 A1 Aug. 13, 2020

Related U.S. Application Data

(60) Provisional application No. 62/545,611, filed on Aug. 15, 2017.

(51) Int. Cl.
*C10G 45/68* (2006.01)
*C10G 69/06* (2006.01)
(Continued)

(52) U.S. Cl.
CPC ............ *C10G 45/68* (2013.01); *C10G 9/36* (2013.01); *C10G 69/06* (2013.01); *C10G 47/18* (2013.01);
(Continued)

(58) Field of Classification Search
None
See application file for complete search history.

(56) References Cited

U.S. PATENT DOCUMENTS

| 6,051,128 A | 4/2000 | Nacamuli et al. |
| 6,190,533 B1 | 2/2001 | Bradow et al. |

(Continued)

FOREIGN PATENT DOCUMENTS

| CN | 1063121 A | 7/1992 |
| WO | WO 2016/054316 A1 | 4/2016 |

(Continued)

OTHER PUBLICATIONS

International Patent Application No. PCT/US2018/046227; Int'l Search Report and the Written Opinion; dated Oct. 30, 2018; 13 pages.

(Continued)

*Primary Examiner* — Tam M Nguyen
(74) *Attorney, Agent, or Firm* — Womble Bond Dickinson (US) LLP

(57) ABSTRACT

Provided are systems and methods for obtaining ethylene and propylene products from, for example, shale gas and shale gas condensate feedstocks. These systems and method operate by utilizing a hydrocracker train to crack C4 and C5 hydrocarbons to a product stream of propane and ethane or using a hydrogenolysis train to process C4 and C5 hydrocarbons to a product stream of propane and ethane that is provided to a cracker for an efficient conversion to ethylene and propylene. The disclosed systems are configured to (Continued)

reduce the amount of offsite hydrogen needed and also provide product streams that include a well-defined set of products as compared to existing approaches.

9 Claims, 2 Drawing Sheets

(51) Int. Cl.
*C10G 9/36* (2006.01)
*C10G 47/18* (2006.01)

(52) U.S. Cl.
CPC ............ *C10G 2300/1025* (2013.01); *C10G 2300/1081* (2013.01); *C10G 2400/02* (2013.01); *C10G 2400/20* (2013.01); *C10G 2400/30* (2013.01)

(56) References Cited

U.S. PATENT DOCUMENTS

| | | | |
|---|---|---|---|
| 6,210,561 B1 | 4/2001 | Bradow et al. | |
| 2013/0131414 A1* | 5/2013 | Iyer | C07C 2/76 585/322 |
| 2013/0217934 A1* | 8/2013 | Chewter | C07C 1/20 585/303 |
| 2013/0233767 A1 | 9/2013 | Shafi et al. | |
| 2014/0100398 A1 | 4/2014 | Jin et al. | |
| 2016/0097007 A1 | 4/2016 | Abudawoud | |
| 2016/0362617 A1* | 12/2016 | Oprins | C10G 11/18 |
| 2016/0369186 A1 | 12/2016 | Dittrich et al. | |
| 2016/0369188 A1* | 12/2016 | Housmans | C10G 67/0445 |
| 2017/0058213 A1* | 3/2017 | Oprins | C10G 45/02 |
| 2017/0058214 A1 | 3/2017 | Oprins et al. | |
| 2017/0121613 A1* | 5/2017 | Oprins | C10G 47/00 |

FOREIGN PATENT DOCUMENTS

| | | |
|---|---|---|
| WO | WO 2016/098909 A1 | 6/2016 |
| WO | WO 2017/001284 A1 | 1/2017 |

OTHER PUBLICATIONS

International Patent Application No. PCT/US2018/046227; Int'l Preliminary Report on Patentability; dated Feb. 27, 2020; 9 pages.
Bruijnincx et al.; "Shale Gas Revolution: An Opportunity for the Production of Biobased Chemicals?"; Angewandte Chemie Int'l Edition; vol. 52; 2013; p. 11980-11987 (Abstract Only).

* cited by examiner

SHALE GAS AND CONDENSATE TO CHEMICALS

CROSS-REFERENCE TO RELATED APPLICATION

This application is the National Stage of International Application No. PCT/US2018/046227 filed Aug. 10, 2018, which claims the benefit of U.S. Provisional Application No. 62/545,611 filed Aug. 15, 2017, the disclosures of which are incorporated herein by this reference in their entireties.

TECHNICAL FIELD

The present application relates to the field of converting shale gas and other feedstocks to other hydrocarbon products, including ethylene and propylene.

BACKGROUND

Within typical cracking complexes, the use of a hydrocracker has historically required as an input hydrogen brought in from outside of the complex. This poses an economic challenge, as hydrogen can be comparatively expensive. Thus, there is a need in the art for hydrocracker systems with a reduced need for offsite hydrogen.

In addition, traditional cracker complexes have also processed feeds by sending feeds to a single cracker (e.g., a liquid, naphtha cracker). This approach, however, results in product streams that include many by-products, and it can be challenging to find a final destination for each one of the many different by-products that are evolved by way of this approach.

Accordingly there is a long-felt need in the art for cracking systems that require a reduced amount of offsite hydrogen and/or that produce product streams that include a well-defined and comparatively small set of products. The value of such systems would be further enhanced if the systems could operate on feeds comprising shale gas and shale gas condensate.

SUMMARY

In meeting the long-felt needs described above, in one aspect, the present disclosure provides methods of producing alkene products from a feedstock (e.g., one comprising an amount of shale gas, shale gas condensate, or both), the methods comprising: separating the feedstock, with a first separation train, into a light feedstock fraction comprising C1-C5 alkanes and a heavy feedstock fraction comprising C6+ alkanes; effecting a cyclization process, with a cyclization train, on the heavy feedstock fraction so as to give rise to one or more of benzene, toluene, xylenes, one or more gasoline range products, and cyclization train hydrogen; removing methane, with a demethanizing train, from the light feedstock fraction so as to give rise to a demethanized light feedstock fraction comprising C2-C5 alkanes; separating, with a second separation train, the demethanized light feedstock fraction so as to separate C2 and C3 alkanes from C4 and C5 alkanes; (i) cracking, with a hydrocracker train, C5 alkanes developed at the second separation train and, optionally C4 alkanes developed at the second separation train, so as to give rise to a hydrocracker product stream comprising C1-C3 alkanes; communicating at least some of the hydrocracker product stream comprising C1-C3 alkanes to the demethanizing train or (ii) processing, with a hydrogenolysis train, C5 alkanes developed at the second separation train and, optionally C4 alkanes developed at the second separation train, so as to give rise to a hydrogenolysis product stream comprising C1-C3 alkanes; communicating at least some of the hydrogenolysis product stream comprising C1-C3 alkanes to the demethanizing train; and cracking, with an alkane cracker train, C2 and C3 alkanes separated at the second separation train so as to give rise to an alkene product stream comprising C2 and C3 alkene; and cracking, with an alkane cracker train, C2 and C3 alkanes separated at the second separation train so as to give rise to an alkene product stream comprising C2 and C3 alkenes.

Also provided are systems, comprising: a first separation train configured to separate a feedstock (e.g., one comprising an amount of shale gas, shale gas condensate, or both), into a light feedstock fraction comprising C1-C5 alkanes and a heavy feedstock fraction comprising C6+ alkanes; a cyclization train configured to process the heavy feedstock fraction so as to give rise to at least benzene, toluene, one or more gasoline range products, and cyclization train hydrogen; a demethanizing train configured to separate methane from the light feedstock fraction so as to give rise to a demethanized light feedstock fraction comprising C2-C5 alkanes; a second separation train configured to separate C2 and C3 alkanes from C4 and C5 alkanes in the demethanized light feedstock fraction; (i) a hydrocracker train configured to crack C5 alkanes developed at the second separation train and, optionally C4 alkanes developed at the second separation train, so as to give rise to a hydrocracker product stream comprising C1-C3 alkanes or (ii) a hydrogenolysis train configured to crack C5 alkanes developed at the second separation train and, optionally C4 alkanes developed at the second separation train, so as to give rise to a hydrogenolysis product stream comprising C1-C3 alkanes; and an alkane cracker train configured to crack C2 and C3 alkanes separated at the second separation train so as to give rise to an alkene product stream comprising C2 and C3 alkenes.

Additionally provided are methods, comprising: (a) from a feedstock (e.g., one that comprises an amount of shale gas, an amount of shale gas condensate, or both), separating C1, C2, C3, C4, and C5 hydrocarbons from C6+ hydrocarbons in the feedstock; (b) (i) cracking, with a hydrocracker train, the C5 hydrocarbons from the feedstock and optionally the C4 hydrocarbons from the feedstock so as to give rise to a hydrocracker product stream comprising C1-C3 alkanes or (ii) processing with a hydrogenolysis train, the C5 hydrocarbons from the feedstock and optionally the C4 hydrocarbons from the feedstock so as to give rise to a hydrocracker product stream comprising C1-C3 alkanes; (c) cracking C2 and C3 hydrocarbons from the feedstock so as to form a final product stream that comprises C2 and C3 alkenes, the final product stream further comprising C2 and C3 alkenes formed from cracking C2 and C3 hydrocarbons from the hydrocracker product stream.

Further disclosed are methods, the methods comprising: with a feedstock comprising at least C1-C6+ hydrocarbons, separating from the feedstock C6+ hydrocarbons and cyclizing the C6+ hydrocarbons in a cyclization train so as to give rise to at least benzene, toluene, and C6-C8 non-aromatic hydrocarbons; and, separating from the feedstock C2-C3 hydrocarbons and cracking in a first cracker train the C2-C3 hydrocarbons so as to give rise to a product set that comprises propylene and ethylene.

Additionally provided are systems, comprising: a first separation configured to split a hydrocarbon feed into a heavy C6+ fraction and a light C5-fraction; a second separation train configured to separate C2-C3 hydrocarbons from the light fraction; a first cracker train configured to crack the C2-C3 hydrocarbons to a product set comprising C2-C3 alkenes; (i) a second cracker train configured to crack at least C4 hydrocarbons of the light C5-fraction to form C1-C3 hydrocarbons or (ii) a first hydrogenolysis train configured to process at least C4 hydrocarbons of the light C5-fraction to form C1-C3 hydrocarbons; and a cyclization train configured to process the C6+ heavy fraction to at least benzene, toluene, and C6-C8 non-aromatic hydrocarbons.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings.

DETAILED DESCRIPTION OF ILLUSTRATIVE ASPECTS

Figure 1:
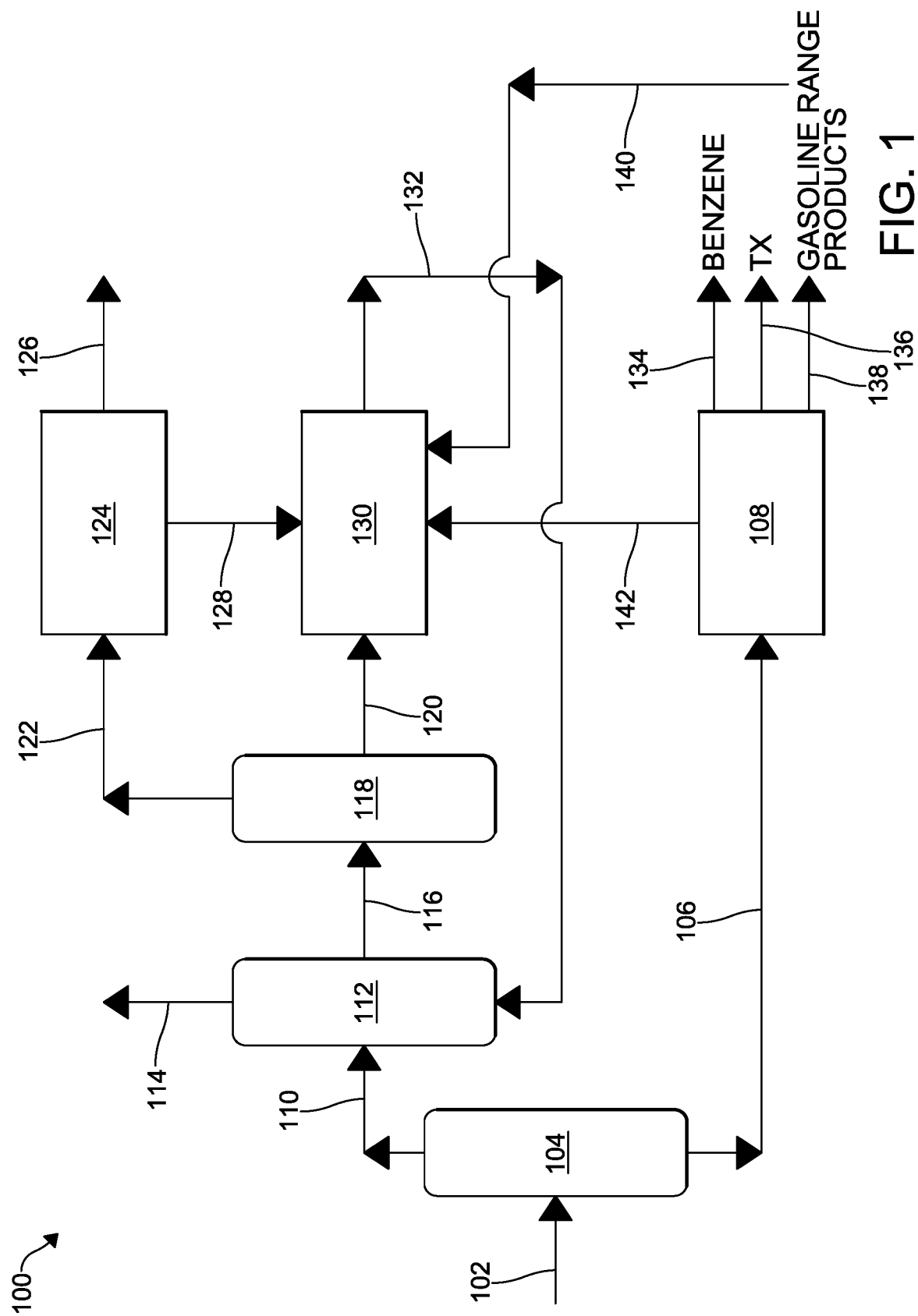
FIG. 1 illustrates an exemplary system according to the present disclosure.

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular aspects by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another aspect includes from the one particular value and/or to the other particular value. Similarly, when values are expressed as approximations, by use of the antecedent "about," it will be understood that the particular value forms another aspect. All ranges are inclusive and combinable, and it should be understood that steps may be performed in any order.

It is to be appreciated that certain features of the disclosure which are, for clarity, described herein in the context of separate aspects, may also be provided in combination in a single aspect. Conversely, various features of the disclosure that are, for brevity, described in the context of a single aspect, may also be provided separately or in any subcombination. Further, reference to values stated in ranges include each and every value within that range. In addition, the term "comprising" should be understood as having its standard, open-ended meaning, but also as encompassing "consisting" as well. For example, a device that comprises Part A and Part B may include parts in addition to Part A and Part B, but may also be formed only from Part A and Part B.

Terms

Provided here are definitions for certain terms used herein.

"Train" refers to one or more modules configured to effect a certain process. For example, a "separation train" may refer to a distillation column (and all associated components, e.g., pumps, reboilers, connectors, and the like), a solid/liquid separator, a cryogenic separator, and the like. A "cyclization train" may refer to an arrangement of modules (e.g., reactors, separators, and the like) configured to effect cyclization reactions on a feed. A "demethanizing train" may refer to an arrangement of separators, columns, chillers, and the like configured to effect removal of methane from a feedstock.

Description

While fracking for shale gas, e.g., methane/ethane/propane, condensate is also collected as a side product. While not a huge portion of the shale gas composition, over time the amount of shale condensate that accumulates can be substantial. At present, however, there is no high value outlet for this shale gas condensate, and there are no entities that use the entire spectrum of shale gas from C1 to C9+. The disclosed technology, however, represents an outlet to utilize the entire shale gas spectrum. The disclosed technology also provides a synergy between the hydrogen produced during a cyclization process and the hydrogen needed for a hydocracking process to produce ethane and propane from C4 and C5 hydrocarbons.

The main products from the aforementioned cyclization process include benzene, TX, and some non-aromatic gasoline range hydrocarbons. The ethane and propane from the hydrocracking process along with the ethane and propane from shale gas are sent to a gas cracker to produce ethylene and propylene, as shown in the attached figures. The principal products from the integrated complex are ethylene, propylene, benzene, TX, and non-aromatic gasoline range hydrocarbons.

The ethane and propane from the hydrocracking process along with the ethane and propane from shale gas are sent to a gas cracker to produce ethylene and propylene. The main products from the integrated complex are ethylene, propylene, benzene, TX (i.e., toluene, xylenes), and non-aromatic gasoline range hydrocarbons. Exemplary cyclization processes include, e.g., SABIC's Light Naphtha Aromatization process or Chevron's Airmax™ process. The hydrocracking process may be performed over a Pt/ZSM-5 catalyst.

Figures

FIG. 1 provides an exemplary system 100. As shown in FIG. 1, feed 102 is provided to first separation train 104. Feed 102 may comprises shale gas and/or shale gas condensate (though this is not a requirement), and may include methane, ethane, propane, butanes, C5 alkanes and C6+ alkanes. First separation train 104 may be operated so as to separate feed 102 into an upper fraction 110 and a lower fraction 106.

In one aspect, the first separation train would be a distillation column that makes a cut based on boiling point between relatively lighter hydrocarbons, i.e., C1-C5, and relatively heavier hydrocarbons, i.e., C6+. The boiling point difference between C5 and C6 is sufficient enough to make this separation of low complexity.

Upper fraction 110 suitably includes C1-C5 species, and C6+ species are suitably included in lower fraction 106. Lower fraction 106 is suitably communicated to cyclization train 108. The cyclization train is suitably operated to give rise to a hydrogen stream 142 and one or more product streams. A cyclization train may include, one or more of, e.g., a reactor, a heater, a compressor, and a downstream separation that includes extraction columns, distillation columns, or both. In the exemplary system of FIG. 1, the product streams 134, 136, and 138 are benzene, TX, and gasoline range products, respectively. It should be understood that the product streams shown in FIG. 1 are illustrative only, and are not limiting of the technology disclosed herein. As an example, system 100 may be configured to produce only one of benzene, toluene, xylenes, gasoline range products, and hydrogen. Alternatively, system 100 may be configured to produce one or more of benzene, toluene, xylenes, gasoline range products, and hydrogen.

Upper fraction 110 from first separation train 104 may be communicated to a demethanizing train 112. The demethanizing train 112 may be operated so as to separate methane in the upper fraction from other species in the upper fraction; as shown in FIG. 1, the demethanizing train 114 may be operated to give rise to a methane stream 114 and a lower stream 116.

Lower stream 116 from the demethanizing train may in turn be communicated to a second separation train 118.

If one seeks only to separate separating C2/C3 from C4/C5, then this may require only a single separation. Depending on the size of the stream, this separation may need take place in multiple columns in parallel. This separation may occur, e.g., under slight vacuum and at below ambient temperatures. The boiling point different between butane (−1 degrees Celsius (° C.)) and propane (−41° C.) is sufficient for a clean separation. Performing this separation is known in the field.

If one seeks to separate C5s and C4s into two independent streams, then a second separation train (described below) may include a series of distillation columns, some of which could be cryogenic separation columns. In such an approach, C5s may be separated using a distillation column. Next, C4s may be separated out from the C2/C3, which separation may occur under slight vacuum and at below ambient temperatures.

Second separation train 118 may be operated so as to separate C2 and C3 species (i.e., ethane, propane) from the C4 and C5 species in the lower stream 116. An upper stream 122 that includes the C2 and C3 species may be communicated to a cracker 124 (e.g., a gas cracker/alkane cracker) that converts the C2 and C3 species in stream 122 to ethylene and propylene, which ethylene and propylene may be taken off in product stream 126. A lower stream 120, comprising C4 and C5 species, may be communicated from the second separation train 118 to hydrocracker train 130.

A hydrocracker train may include, e.g., one or more reactors, such as adiabatic reactors including interstage coolers to cool products exiting a reactor before entering a subsequent reactor. The reactors could either be fixed-bed or radial flow reactors. The hydrocracker train may comprise compressors, pumps, and the like. A separation section for excess hydrogen and unreacted C4/C5 species may also be included, with any of the separated materials being recycled back to the inlet reactor flow.

As shown in FIG. 1, hydrogen evolved at cracker 124 (e.g., alkane cracker) may be communicated via a hydrogen stream 128 to hydrocracker train 130. In addition, gasoline range products from cyclization train 108 may be communicated via gasoline range product stream 140 to hydrocracker train 130. Hydrogen stream 142 may also be communicated from cyclization train 108 to hydrocracker train 130. Thus, hydrocracker 130 may receive hydrogen from (e.g., alkane) cracker 124 and from cyclization train 108.

Some or all of the hydrogen required by hydrocracker train 130 may be provided by hydrogen stream 142 and hydrogen stream 128, although this is optional. (In some aspects, none of the hydrogen required by hydrocracker train 130 is supplied by hydrogen stream 142 and hydrogen stream 128.) For example, the hydrogen supplied to hydrocracker train 130 by hydrogen stream 128 and hydrogen stream 142 may be from about 1 to about 100% of the hydrogen utilized by hydrocracker train 130, e.g., from about 1 to about 100%, from about 5 to about 95%, from about 10 to about 90%, from about 15 to about 85%, from about 20 to about 80%, from about 25 to about 75%, from about 30 to about 65%, from about 35 to about 60%, from about 35 to about 55%, from about 40 to about 50%, or even about 45% of the hydrogen utilized by hydrocracker train 130.

In some aspects, from about 1 to about 100% (e.g., from about 1 to about 100%, from about 5 to about 95%, from about 10 to about 90%, from about 15 to about 85%, from about 20 to about 80%, from about 25 to about 75%, from about 30 to about 65%, from about 35 to about 60%, from about 35 to about 55%, from about 40 to about 50%, or even about 45%) of the hydrogen utilized by the hydrocracker train 130 may be provided by hydrogen stream 128 from (e.g., alkane) cracker 124.

Similarly, from about 1 to about 100% (e.g., from about 1 to about 100%, from about 5 to about 95%, from about 10 to about 90%, from about 15 to about 85%, from about 20 to about 80%, from about 25 to about 75%, from about 30 to about 65%, from about 35 to about 60%, from about 35 to about 55%, from about 40 to about 50%, or even about 45%) of the hydrogen utilized by the hydrocracker train 130 may be provided by hydrogen stream 142 from cyclization train 108.

The ratio (by weight) of the hydrogen flowrate of hydrogen stream 128 to the hydrogen flowrate of hydrogen stream 142 may, in some aspects, be from about 1:1000 to about 1000:1, e.g., from about 1:1000 to about 1000:1, from about 1:100 to about 100:1, from about 1:10 to 10:1, or even from about 1:5 to about 5:1. It is not a requirement that all of the hydrogen evolved by cracker 124 or all of the hydrogen evolved by cyclization train 108 be communicated to hydrocracker train 130, as from about 1 to about 100% of the hydrogen evolved in either or both of cracker 124 and cyclization train 108 may be communicated to hydrocracker train 130.

Hydrocracker train 130 may be operated to crack the C4 and C5 species down to C1-C3 species, which may be removed via stream 132. Stream 132, comprising C1-C3 species, may be communicated to demethanizing train 112, which demethanizing train may be operated to remove methane from stream 132. As described elsewhere herein, hydrocracker train 130 may, optionally, be substituted by a hydrogenolysis train.

Figure 2:
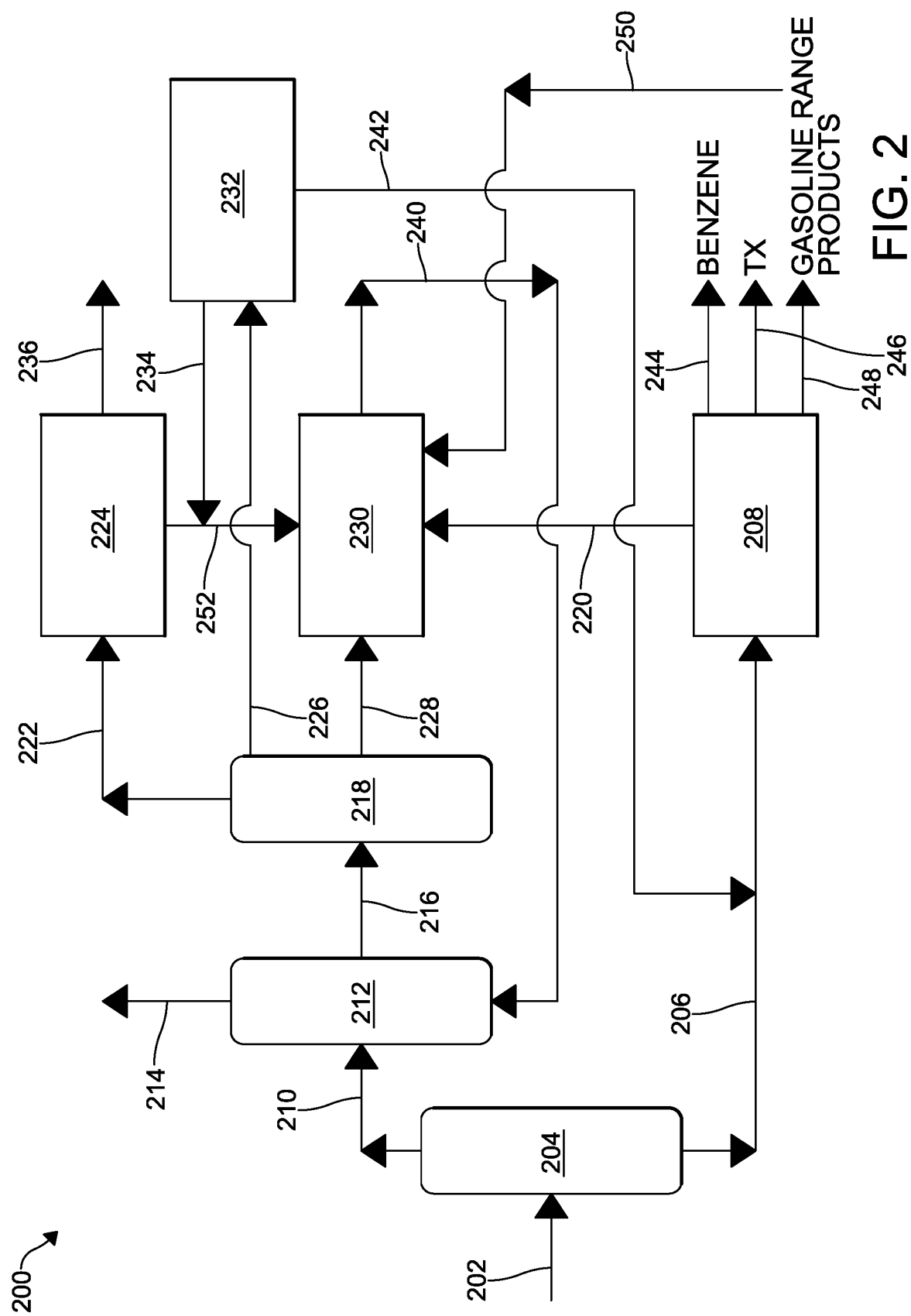
FIG. 2 illustrates an alternative exemplary system according to the present disclosure.

FIG. 2 provides an alternative exemplary system 200. As shown in FIG. 2, feed 202 is provided to first separation train 204. Feed 202 suitably comprises shale gas and/or shale gas condensate (though this is not a requirement), and may include methane, ethane, propane, butanes, C5 alkanes and C6+ alkanes. First separation train 204 may be operated so as to separate feed 202 into an upper fraction 210 and a lower fraction 206. Upper fraction 210 suitably includes C1-C5 species, and C6+ species are suitably included in lower fraction 206. Lower fraction 206 is suitably communicated to cyclization train 208, which cyclization train is suitably operated to give rise to a hydrogen stream 220 and one or more product streams. In the exemplary system of FIG. 2, the product streams 244, 246, and 248 are benzene, TX, and gasoline range products, respectively. It should be understood that the product streams shown in FIG. 2 are illustrative only, and are not limiting of the technology disclosed herein. As an example, system 200 may be configured to produce only one of benzene, toluene, xylenes, gasoline range products, and hydrogen. Alternatively, system 200 may be configured to produce one or more of benzene, toluene, xylenes, gasoline range products, and hydrogen.

The upper fraction 210 from first separation train 204 may be communicated to a demethanizing train 212. The demethanizing train 212 may be operated so as to separate methane in the upper fraction from other species in the upper fraction; as shown in FIG. 2, the demethanizing train 214 may be operated to give rise to a methane stream 214 and a lower stream 216.

Lower stream 216 from the demethanizing train may in turn be communicated to a second separation train 218. The second separation train 218 may be operated so as to separate C2 and C3 species (i.e., ethane, propane) from the C4 and C5 species in lower stream 216. An upper stream 222 that includes the C2 and C3 species may be communicated to a cracker 224 (e.g., a gas cracker/alkane cracker) that converts the C2 and C3 species in stream 222 to ethylene and propylene, which ethylene and propylene may be taken off in product stream 236. A middle stream 226, comprising C4 species, may be communicated from the second separation train 218 to dehydrogenation and metathesis train 232. A lower stream 228, comprising C5 species, may be communicated to hydrocracker train 230.

Dehydrogenation and metathesis train 232 may be operated on the C4 species provided in stream 226 to give rise to at least propylene and hexene, e.g., 3-hexene. The propylene may be communicated via stream 238 to be part of the system product stream. The evolved hexene may be communicated to cyclization train 208 via stream 242. (Dehydrogenation and metathesis train 232 may also evolve a hydrogen stream 234.)

As shown in FIG. 2, hydrogen evolved at (e.g., alkane) cracker 224 may be communicated via a hydrogen stream 252 to hydrocracker train 230. In addition, gasoline range products from cyclization train 208 may be communicated via gasoline range product stream 250 to hydrocracker train 230. Hydrogen stream 220 may also be communicated from cyclization train 208 to hydrocracker train 230.

Hydrocracker train 230 may be operated to crack C5 species 228 and gasoline range product species 250 down to C1-C3 species, which may be removed via stream 240. Stream 240, comprising C1-C3 species, may be communicated to demethanizing train 212, which demethanizing train may be operated to remove methane from stream 240. (As described elsewhere herein, hydrocracker train 230 may, optionally, be substituted by a hydrogenolysis train.)

Illustrative Aspects

For n-pentane, product yields achieved through steam cracking are approximately 34 wt % ethylene and 21 wt % propylene (total 55 wt %). Assuming a n-pentane hydrocracking product distribution of 7.6 wt % methane, 37.8 wt % ethane, 54.6 wt % propane, and this product distribution is then sent to the steam cracker furnaces, then the production yields achieved from the steam cracker are 54 wt % ethylene and 10 wt % propylene (total 64%). By performing the hydrocracking, the combined yield of ethylene and propylene may increase by 9%. The product yield also may shift towards ethylene, which is of higher value than propylene.

For n-butane, product yields achieved through steam cracking are approximately 46 wt % ethylene and 20 wt % propylene (total 66 wt %). Assuming a n-butane hydrocracking product distribution of 3.8 wt % methane, 22.4 wt % ethane, 73.8 wt % propane, and this product distribution is sent to the steam cracker furnaces, then the production yields achieved from the steam cracker may be 52% ethylene and 13% propylene (total 65%). By performing the hydrocracking, the yield of ethylene may increase by 6% (assuming the foregoing specific hydrocracking distribution).

TABLE 1

Exemplary Product Distributions

| Method | Ethylene | Propylene | Total |
|---|---|---|---|
| n-butane steam cracking | 46 wt % | 20% | 66 wt % |
| n-butane hydrocracking (present disclosure) | 52 wt % | 13 wt % | 65 wt % |
| n-pentane steam cracking | 34 wt % | 21 wt % | 55 wt % |
| n-pentane hydrocracking (present disclosure) | 54 wt % | 10 wt % | 64 wt % |

As shown, the disclosed technology has the effects of (1) increasing the overall yield of ethylene and propylene from an alkane feedstock; and (2) increasing the relative amount of ethylene in the ethylene/propylene products of processing that alkane feedstock.

Without being bound to any particular theory, the foregoing improvements may be based on the assumption that within a steam cracker (a pyrolysis reaction that operates under the assumption of free radical chemistry), shorter chain hydrocarbons like ethane/propane are converted to ethylene/propylene more efficiently than longer chain hydrocarbons. This may be due to the relatively higher number of fragmentation reactions that occur for C4/C5 hydrocarbons, which in turn result in forming more free radical fragments, and given this higher number of free radical fragments, a variety of other products can form. As an example, a C5 hydrocarbon can form a C5 radical, a C4 radical, a C3 radical, a C2 radical, and a C1 radical. A C2 species, however, can only form a C2 radical and a C1 radical.

Exemplary Aspects

The following aspects are exemplary only and do not limit the scope of the present disclosure or the appended claims.

Aspect 1. A method of producing alkene products from a feedstock (e.g., one comprising an amount of shale gas, shale gas condensate, or both), the method comprising, consisting of or consisting essentially of: separating the feedstock, with a first separation train, into a light feedstock fraction comprising C1-C5 alkanes and a heavy feedstock fraction comprising C6+ alkanes; effecting a cyclization process, with a cyclization train, on the heavy feedstock fraction so as to give rise to one or more of benzene, toluene, xylenes, one or more gasoline range products (e.g., C6-C8 non-aromatic hydrocarbons), and cyclization train hydrogen; removing methane, with a demethanizing train, from the light feedstock fraction so as to give rise to a demethanized light feedstock fraction comprising C2-C5 alkanes;

separating, with a second separation train, the demethanized light feedstock fraction so as to separate C2 and C3 alkanes from C4 and C5 alkanes; (i) cracking, with a hydrocracker train, C5 alkanes developed at the second separation train and, optionally C4 alkanes developed at the second separation train, so as to give rise to a hydrocracker product stream comprising C1-C3 alkanes; communicating at least some of the hydrocracker product stream comprising C1-C3 alkanes to the demethanizing train or (ii) processing, with a hydrogenolysis train, C5 alkanes developed at the second separation train and, optionally C4 alkanes developed at the second separation train, so as to give rise to a hydrogenolysis product stream comprising C1-C3 alkanes; communicating at least some of the hydrogenolysis product stream comprising C1-C3 alkanes to the demethanizing train; and cracking, with an alkane cracker train, C2 and C3 alkanes separated at the second separation train so as to give rise to an alkene product stream comprising C2 and C3 alkenes; and cracking, with an alkane cracker train, C2 and C3 alkanes separated at the second separation train so as to give rise to an alkene product stream comprising C2 and C3 alkenes.

The feedstock may comprise pure shale gas, pure shale gas condensate, or both. It is not a requirement that the feedstock comprise pure shale gas or pure shale gas condensate, as the feedstock may comprise shale gas or condensate that has been processed before introduction to the first separation train. The relative amounts of the light and heavy feedstock fractions may be dictated by the relative amounts of C1-C5 and C6+ alkanes in the feedstock.

The first separation train may comprise, e.g., one or more distillation columns. Suitable columns will be known to those in the art and are described elsewhere herein.

The cyclization train may include, e.g., an aromatization unit and a separations unit; suitable cyclization trains are described elsewhere herein. The cyclization train may be operated so as to yield at least benzene, toluene, xylenes, one or more gasoline range products (e.g., C6-C8 non-aromatic hydrocarbons) and cyclization train hydrogen. The relative amounts of the foregoing may be dictated by the composition of the C6+ alkane stream fed to the cyclization train, as well as the conditions of the cyclization train.

The demethanizing train may include, e.g., a cryogenic separation unit or units, as known in the art. As described, the demethanizing train may be operated so as to give rise to a methane stream and a stream (which may be termed a demethanized light feedstock fraction) that comprises C2-C5 alkanes.

The C2-C5 stream may be processed by a second separation train so as to separate C2 and C3 alkanes from C4 and C5 alkanes. Suitable second separation trains are described elsewhere herein. For example, if one may wish to separate C5s and C4s into two independent streams, a second separation train may include a series of distillation columns, some of which could be cryogenic separation columns. In such an approach, C5s may be separated using a distillation column. Next, C4s may be separated out from the C2/C3, which separation may occur under slight vacuum and at below ambient temperatures. Alternatively, a distillation column may be used to separate C2/C3 from C4/C5.

C5 alkanes (and, optionally, C4 alkanes) developed at the second separation train may be cracked at a hydrocracker train so as to give rise to a hydrocracker product stream that includes C1-C3 alkanes Cracking is known to those of skill in the art, and may be performed over, e.g., a Pt/ZSM-5 catalyst. Pt loading may be, e.g., between 0.05 and 0.5 wt %, and the Si/Al ratio of the zeolite may be between about 20-100. Some of the hydrocracker product stream may be communicated to the demethanizing train.

Using an alkane cracker train, C2 and C3 alkanes obtained at the second separation train may be cracked so as to give rise to an alkene product stream that comprises ethylene and propylene. As example, the alkane cracker train may be, e.g., an ethane/propane gas cracker (E/P Gas Cracker). This may have steam cracker furnaces, gas/liquid separation units, compressors, pumps, separation units for products, which are known to those of skill in the art.

An alkene product stream may be from, e.g., about 45 to about 85 weight percent (wt %) ethylene, and from about 2 to about 20 wt % propylene. An alkene product stream may further include, in some aspects, e.g., butadiene, isobutylene, butene, and/or pygas. C4 olefins may be hydrogenated and recycled back to the hydrocracking reactor. Pygas may be sent to a cyclization separation train where benzene, toluene, xylenes would be separated out from non-aromatics.

In some aspects, the hydrocracker train may, optionally, be substituted by a hydrogenolysis train, which hydrogenolysis train may be used to process C4 and/or C5 species. A hydrogenolysis train may include a hydrogenolysis reactor. A hydrogenolysis train may also comprise a dehydrogenation reactor, isomerization reactor, or any combination thereof.

In aspects that comprise a hydrogenolysis train in place of a hydrocracking train, the hydrogenolysis train may use the same input streams and/or materials. The hydrogenolysis train may also yield the same products as the hydrocracker train, e.g., i.e. C1-C3 alkanes may be produced by the hydrogenolysis train. The hydrogenolysis train may also have hydrogen as an input.

Suitable catalysts for a hydrogenolysis train include, for example, the following metals either alone or as a bimetallic combination supported on alumina ($Al_2O_3$), Silica ($SiO_2$), or titania ($TiO_2$): Pt, Ir, Ru, Rh, $Mo_2C$, MoC, Re, and the like.

Aspect 2. The method of Aspect 1, further comprising communicating at least some of the cyclization train hydrogen to the hydrocracker train. In some aspects, from about 10 to about 90 wt % of the hydrogen from the cyclization train is communicated to the hydrocracker train, e.g., from about 10 to about 90 wt %, from about 15 to about 85 wt %, from about 20 to about 80 wt %, from about 25 to about 75 wt %, from about 30 to about 70 wt %, from about 35 to about 65 wt %, from about 40 to about 60 wt %, from about 45 to about 55 wt %, or even about 50 wt %.

Aspect 3. The method of any of Aspects 1-2, further comprising combusting at least some of the methane removed by the demethanizing train. This may be performed so as to supply energy to one or more of the first separation train, the cyclization train, the second separation train, the alkane cracker train, or any other process module. (The methane may also be combusted to provide necessary energy to the demethanizing train.)

Aspect 4. The method of Aspect 3, wherein combusting the methane provides 75% or more of the heat utilized by one or more of the first separation train, the cyclization train, the second separation train, or the alkane cracker train. In some aspects, combusting methane removed by the demethanizing train provides 75-100%, 80-95%, 85-90%, or even about 90% of the heat utilized by one or more of the first separation train, the cyclization train, the second separation train, the hydrogenolysis train, or the alkane cracker train. In some aspects, combusting the methane provides within about 10% of the heat utilized by one or more of the first separation train, the cyclization train, the second separation train, the hydrogenolysis train, or the alkane cracker train Aspect 5. The method of any of Aspects 1-4, wherein the alkane cracker train is characterized as a gas cracker.

Aspect 6. The method of any of Aspects 1-5, further comprising communicating, to the hydrocracker train or hydrogenolysis train, whichever present, at least some of the gasoline range products from the cyclization train. From about 1 to about 100% of the gasoline range products may be communicated from the cyclization train to the hydrocracker train or hydrogenolysis train, e.g., from about 1 to about 100%, from about 5 to about 95%, from about 10 to about 90%, from about 15 to about 85%, from about 20 to about 80%, from about 25 to about 75%, from about 30 to about 70%, from about 35 to about 70%, from about 40 to about 65%, from about 45 to about 60%, or even from about 50 to about 55%.

The method may further comprise cracking and/or effecting hydrogenolysis on the gasoline range products to form methane and C2-C3 alkanes.

Aspect 7. The method of any of Aspects 1-6, further comprising effecting dehydrogenation and metathesis on C4 alkanes developed at the second separation train to give rise to C2 and/or C3 alkenes and optionally hexenes (e.g., 3-hexene). One may also, optionally, effect dehydrogenation on the C4 alkanes.

Aspect 8. The method of Aspect 7, further comprising communicating (e.g., to another process module) hydrogen evolved in the dehydrogenation to the hydrocracker train or the hydrogenolysis train, whichever present. The method may include communicating up to 100% of the hydrogen evolved in the dehydrogenation to the hydrocracker (or hydrogenolysis) train, e.g., 5, 10, 15, 20, 25, 30, 35, 40, 45, 50, 55, 60, 65, 70, 75, 80, 85, 90, 95, or even 100% of the hydrogen. In some aspects, however, no hydrogen evolved within the system is communicated to the hydrocracker (or hydrogenolysis) train.

Aspect 9. The method of any of Aspects 7-8, further comprising communicating, to the cyclization train, hexene or other products evolved by the metathesis when metathesis is performed. In some aspects, the output of the metathesis process may comprise unreacted butenes, and 2-pentene. Products formed in the olefin metathesis step may go through the appropriate downstream separations train, with undesired olefins recycled back through the metathesis reactor, which olefins may be recycled to extinction. C4-C6 olefins may undergo a double bond shift to form other isomers, which shift may be controlled by proper choice of catalyst and conditions. Butenes may be recycled to an isomerization unit to generate the desired ratio of 1-butene and 2-butene, depending on the process.

Aspect 10. A system, comprising, consisting of or consisting essentially of: a first separation train configured to separate a feedstock (e.g., one comprising an amount of shale gas, shale gas condensate, or both), into a light feedstock fraction comprising C1-C5 alkanes and a heavy feedstock fraction comprising C6+ alkanes; a cyclization train configured to process the heavy feedstock fraction so as to give rise to at least benzene, toluene, xylenes, one or more gasoline range products, and cyclization train hydrogen; a demethanizing train configured to separate methane from the light feedstock fraction so as to give rise to a demethanized light feedstock fraction comprising C2-C5 alkanes; a second separation train configured to separate C2 and C3 alkanes from C4 and C5 alkanes in the demethanized light feedstock fraction; (i) a hydrocracker train configured to crack C5 alkanes developed at the second separation train and, optionally C4 alkanes developed at the second separation train, so as to give rise to a hydrocracker product stream comprising C1-C3 alkanes or (ii) a hydrogenolysis train configured to process C5 alkanes developed at the second separation train and, optionally C4 alkanes developed at the second separation train, so as to give rise to a hydrogenolysis product stream comprising C1-C3 alkanes; an alkane cracker train configured to crack C2 and C3 alkanes separated at the second separation train so as to give rise to an alkene product stream comprising C2 and C3 alkenes.

Suitable first separation trains are described elsewhere herein. Also described elsewhere herein are exemplary cyclization trains, demethanizing trains, second separation trains, hydrocracker trains, hydrogenolysis trains, and alkane cracker trains.

Aspect 11. The system of Aspect 10, wherein the cyclization train comprises an aromatization sub-train and a separations sub-train, the separations train being configured to separate benzene from toluene and xylene evolved in the cyclization train.

Aspect 12. The system of any of Aspects 10-11, wherein the system is configured to communicate hydrogen evolved at the cyclization train to the hydrocracker train or the hydrogenolysis train, whichever present.

Aspect 13. The system of any of Aspects 10-12, wherein the system is configured to communicate gasoline range products evolved at the cyclization train to the hydrocracker train or the hydrogenolysis train, whichever present, such that the communicated gasoline range products are cracked or hydrogenolysed to C1-C3 alkanes. (Gasoline range products are described elsewhere herein.)

Aspect 14. The system of any of Aspects 10-13, further comprising a metathesis train configured to effect metathesis on C4 alkanes developed at the second separation train so as to give rise to C2 and C3 alkenes, the metathesis train optionally comprising a hydrogenation sub-train.

Aspect 15. The system of Aspect 14, (a) the system being configured to communicate hydrogen evolved at the metathesis train to the hydrocracker train or to the hydrogenolysis train, whichever present, (b) the system being configured to communicate hexene evolved at the metathesis train to the cyclization train, or (a) and (b).

Aspect 16. A method, comprising, consisting of or consisting essentially of: (a) from a feedstock (e.g., one that comprises an amount of shale gas, an amount of shale gas condensate, or both), separating C1, C2, C3, C4, and C5 hydrocarbons from C6+ hydrocarbons in the feedstock; (b) (i) cracking, with a hydrocracker train, the C5 hydrocarbons from the feedstock and optionally the C4 hydrocarbons from the feedstock so as to give rise to a hydrocracker product stream comprising C1-C3 alkanes or (ii) processing with a hydrogenolysis train, the C5 hydrocarbons from the feedstock and optionally the C4 hydrocarbons from the feedstock so as to give rise to a hydrogenolysis product stream comprising C1-C3 alkanes; (c) cracking C2 and C3 hydrocarbons from the feedstock so as to form a final product stream that comprises C2 and C3 alkenes, the final product stream further comprising C2 and C3 alkenes formed from cracking C2 and C3 hydrocarbons from the hydrocracker product stream.

Aspect 17. The method of Aspect 16, further comprising effecting dehydrogenation and metathesis on C4 alkanes of the feedstock so as to give rise to additional C2 and C3 alkenes, the final product stream optionally comprising the additional C2 and C3 alkenes.

Aspect 18. The method of any of Aspects 16-17, further comprising effecting cyclization of C6+ hydrocarbons of the feedstock.

Aspect 19. The method of Aspect 18, further comprising, at step (b), cracking gasoline range products of the cyclization or, optionally, effecting hydrogenolysis on gasoline range products of the cyclization Aspect 20. The method of any of Aspects 16-19, further comprising separating methane from the feedstock, and, optionally, combusting at least some of the methane so as to supply heat to one or more of steps (a), (b), or (c).

Aspect 21. A method, comprising, consisting of or consisting essentially of: with a feedstock comprising at least C1-C6+ hydrocarbons, separating from the feedstock C6+ hydrocarbons and cyclizing the C6+ hydrocarbons in a cyclization train to as to give rise to at least benzene, toluene, and C6-C8 non-aromatic hydrocarbons; and, separating from the feedstock C2-C3 hydrocarbons and (i) cracking in a first cracker train or (ii) processing in a hydrogenolysis train the C2-C3 hydrocarbons so as to give rise to a product set that comprises propylene and ethylene.

Aspect 22. The method of Aspect 21, further comprising separating from the feedstock C4 and C5 hydrocarbons and cracking in a second cracker train at least the C5 hydrocarbons so as to form C1-C3 hydrocarbons. Alternatively, one may separate from the feedstock C4 and C5 hydrocarbons and effect hydrogenolysis with a hydrogenolysis train on at least the C5 hydrocarbons so as to form C1-C3 hydrocarbons Aspect 23. The method of Aspect 22, further comprising cracking in the second cracker train the C4 hydrocarbons so as to form C1-C3 hydrocarbons. Alternatively, one may separate from the feedstock the C4 hydrocarbons and effect hydrogenolysis with a hydrogenolysis train on at least the C4 hydrocarbons so as to form C1-C3 hydrocarbons.

Aspect 24. The method of any of Aspects 22-23, further comprising effecting dehydrogenation and metathesis on the C4 hydrocarbons so as to give rise to propylene, hexene, and hydrogen, and further comprising including at least some of the propylene in the product set and still further optionally communicating at least some of the hexene to the cyclization train.

Aspect 25. The method of any of Aspects 22-24, further comprising supplying to the second cracker train or to the hydrogenolysis train, whichever present, hydrogen evolved from the cyclizing, hydrogen evolved at the first cracker train, or both.

Aspect 26, the method of any of Aspects 21-25, further comprising communicating hydrogen evolved during the dehydrogenation and metathesis to the cyclization train.

Aspect 27. The method of any of Aspects 23-29, wherein the product set is at least 60 wt % ethylene and propylene.

Aspect 28. The method of any of Aspects 23-30, wherein the product set is at least 47 wt % ethylene.

Aspect 29. The method of any of Aspects 23-31, wherein the product set is at least 50 wt % ethylene.

Aspect 30. The method of any of Aspects 23-32, wherein the product set is less than 20 wt % propylene.

Aspect 31. The method of any of Aspects 23-33, wherein the product set is less than 20 wt % propylene and more than 45 wt % ethylene.

Aspect 32. A system, comprising, consisting of or consisting essentially of: a first separation train configured to split a hydrocarbon feed into a heavy C6+ fraction and a light C5-fraction; a second separation train configured to separate C2-C3 hydrocarbons from the light fraction; a first cracker train configured to crack the C2-C3 hydrocarbons to a product set comprising C2-C3 alkenes;(i) a second cracker train configured to crack at least C4 hydrocarbons of the light C5-fraction to form C1-C3 hydrocarbons or (ii) a first hydrogenolysis train configured to process at least C4 hydrocarbons of the light C5-fraction to form C1-C3 hydrocarbons; and a cyclization train configured to process the C6+ heavy fraction to at least benzene, toluene, and C6-C8 non-aromatic hydrocarbons.

Aspect 33. The system of Aspect 32, further comprising a dehydrogenation and metathesis train configured to process the C4 hydrocarbons of the light C5-fraction so as to give rise to propylene, hexene, and hydrogen.

Aspect 34. The system of Aspect 33, the system being configured to communicate hydrogen evolved at the dehydrogenation and metathesis train to the second cracker train and/or to the first hydrogenolysis train, whichever present.

Aspect 35. The system of any of Aspects 33-34, the system being configured to communicate hexene evolved at the dehydrogenation and metathesis train to the cyclization train.

Aspect 36. The system of any of Aspects 32-35, the system being configured to communicate hydrogen evolved at the first cracker train to the second cracker train or to the first hydrogenoloysis train, whichever present.

Aspect 37. The system of any of Aspects 33-36, the system being configured to provide a product set that is at least 60 wt % ethylene and propylene.

Aspect 38. The system of any of Aspects 33-37, the system being configured to provide a product set that is at least 47 wt % ethylene.

Aspect 39. The system of any of Aspects 32-38, the system being configured to provide a product set that is at least 50 wt % ethylene.

Aspect 40. The system of any of Aspects 32-39, the system being configured to provide a product set that is less than 20 wt % propylene.

Aspect 41. The system of any of Aspects 32-40, the system being configured to provide a product set that is less than 20 wt % propylene and more than 45 wt % ethylene.

What is claimed:
1. A method of producing alkene products from a feedstock, the method comprising:
   separating the feedstock, with a first separation train, into a light feedstock fraction comprising C1-C5 alkanes and a heavy feedstock fraction comprising C6+ alkanes;
   effecting a cyclization process, with a cyclization train, on the heavy feedstock fraction so as to give rise to one or more of least benzene, toluene, xylenes, one or more gasoline range products, and cyclization train hydrogen;
   removing methane, with a demethanizing train, from the light feedstock fraction so as to give rise to a demethanized light feedstock fraction comprising C2-C5 alkanes;
   separating, with a second separation train, the demethanized light feedstock fraction so as to separate C2 and C3 alkanes from C4 and C5 alkanes;
   (i) cracking, with a hydrocracker train, C5 alkanes developed at the second separation train and, optionally C4 alkanes developed at the second separation train, so as to give rise to a hydrocracker product stream comprising C1-C3 alkanes and communicating at least some of the hydrocracker product stream comprising C1-C3 alkanes to the demethanizing train or

(ii) processing, with a hydrogenolysis train, C5 alkanes developed at the second separation train and, optionally C4 alkanes developed at the second separation train, so as to give rise to a hydrogenolysis product stream comprising C1-C3 alkanes and communicating at least some of the hydrogenolysis product stream comprising C1-C3 alkanes to the demethanizing train; and cracking, with an alkane cracker train, C2 and C3 alkanes separated at the second separation train so as to give rise to an alkene product stream comprising C2 and C3 alkenes; and cracking, with an alkane cracker train, C2 and C3 alkanes separated at the second separation train so as to give rise to an alkene product stream comprising C2 and C3 alkenes.

2. The method of claim 1, further comprising communicating at least some of the cyclization train hydrogen to the hydrocracker train.

3. The method of claim 1, further comprising combusting at least some of the methane removed by the demethanizing train so as to supply heat to one or more of the first separation train, the cyclization train, the demethanizing train, the second separation train, and the alkane cracker train.

4. The method of claim 3, wherein combusting the methane provides within about 10% of the heat utilized by one or more of the first separation train, the cyclization train, the demethanizing train, the second separation train, and the alkane cracker train.

5. The method of claim 1, wherein the alkane cracker train is characterized as a gas cracker.

6. The method of claim 1, further comprising communicating, to the hydrocracker train or to the hydrogenolysis train, whichever present, at least some of the gasoline range products from the cyclization train, and further comprising cracking or effecting hydrogenolysis on the gasoline range products to form methane and C2-C3 alkanes.

7. The method of claim 1, further comprising effecting dehydrogenation and metathesis on C4 alkanes developed at the second separation train so as to give rise to one or both of C2 and C3 alkenes.

8. The method of claim 7, further comprising communicating hydrogen evolved in the dehydrogenation, metathesis, or both, to the hydrocracker train or the hydrogenolysis train, whichever present.

9. The method of claim 7, further comprising communicating, to the cyclization train, hexene evolved by the metathesis.

\* \* \* \* \*